United States Patent
Lee

(10) Patent No.: US 11,013,841 B2
(45) Date of Patent: May 25, 2021

(54) CENTRIFUGAL-DIALYSATE-FLOW HEMODIALIZER

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 81 days.

(21) Appl. No.: 16/586,970

(22) Filed: Sep. 28, 2019

(65) Prior Publication Data

US 2021/0093769 A1  Apr. 1, 2021

(51) Int. Cl.
| | |
|---|---|
| *A61M 1/16* | (2006.01) |
| *A61M 1/26* | (2006.01) |
| *B01D 69/08* | (2006.01) |
| *B01D 65/08* | (2006.01) |
| *B01D 63/02* | (2006.01) |

(52) U.S. Cl.
CPC .......... *A61M 1/1625* (2014.02); *A61M 1/262* (2014.02); *B01D 63/02* (2013.01); *B01D 65/08* (2013.01); *B01D 69/082* (2013.01); *A61M 2206/12* (2013.01); *B01D 69/081* (2013.01); *B01D 2313/20* (2013.01)

(58) Field of Classification Search
CPC ................ A61M 1/1625; A61M 1/262; A61M 2206/12; B01D 63/02; B01D 65/08; B01D 69/082; B01D 2313/20; B01D 69/081
See application file for complete search history.

(56) References Cited

U.S. PATENT DOCUMENTS

| | | | |
|---|---|---|---|
| 3,422,008 A | 1/1969 | McLain | |
| 3,536,611 A | 10/1970 | De Filippi et al. | |
| 3,616,928 A | 11/1971 | Rosenblatt | |
| 4,002,567 A | 1/1977 | Konno et al. | |
| 4,451,369 A | 5/1984 | Sekino et al. | |
| 4,666,469 A | 5/1987 | Krueger et al. | |
| 4,758,341 A | 7/1988 | Banner | |
| 5,263,924 A * | 11/1993 | Mathewson | B01D 63/02 604/6.14 |
| 5,830,370 A * | 11/1998 | Maloney, Jr. | B01D 63/02 210/780 |
| 6,379,618 B1 * | 4/2002 | Piplani | A61M 1/1629 422/45 |
| 6,641,731 B1 * | 11/2003 | Heilmann | B01D 46/0004 210/321.79 |

(Continued)

FOREIGN PATENT DOCUMENTS

| | | |
|---|---|---|
| JP | 0464737 B1 | 12/1994 |
| WO | 2014202710 A1 | 12/2014 |
| WO | 2018060510 A2 | 5/2018 |

*Primary Examiner* — Krishnan S Menon

(57) ABSTRACT

To enhance diffusive mass transfer of solutes, the present hemodialyzer in a cylindrical configuration for hemodialysis comprises a blood compartment having a packed bundle of hollow fibers in a reversibly distensible doughnut configuration on a radial cross-section, and a dialysate compartment having an axial spiral flow converter slidably inserted in a center of the packed bundle of the hollow fibers and an outer circumferential space encircling an outer circumferential layer of the packed bundle of the hollow fibers. The axial spiral flow converter is configured to convert an axial dialysate flow to a centrifugal dialysate flow radially spreading from the center of the packed bundle of the hollow fibers to the outer circumferential space of the hemodialyzer.

12 Claims, 12 Drawing Sheets

(56) References Cited

U.S. PATENT DOCUMENTS

| | | | |
|---|---|---|---|
| 7,220,435 B2 * | 5/2007 | Dastidar | A61K 31/198 424/489 |
| 9,186,629 B2 | 11/2015 | Mahley et al. | |
| 2008/0199357 A1 * | 8/2008 | Gellman | A61M 1/1698 422/48 |
| 2008/0234623 A1 * | 9/2008 | Strauss | B01D 63/02 604/6.11 |
| 2010/0170850 A1 | 7/2010 | Heilmann et al. | |
| 2016/0095969 A1 * | 4/2016 | Maurer | A61M 1/1623 422/48 |

* cited by examiner

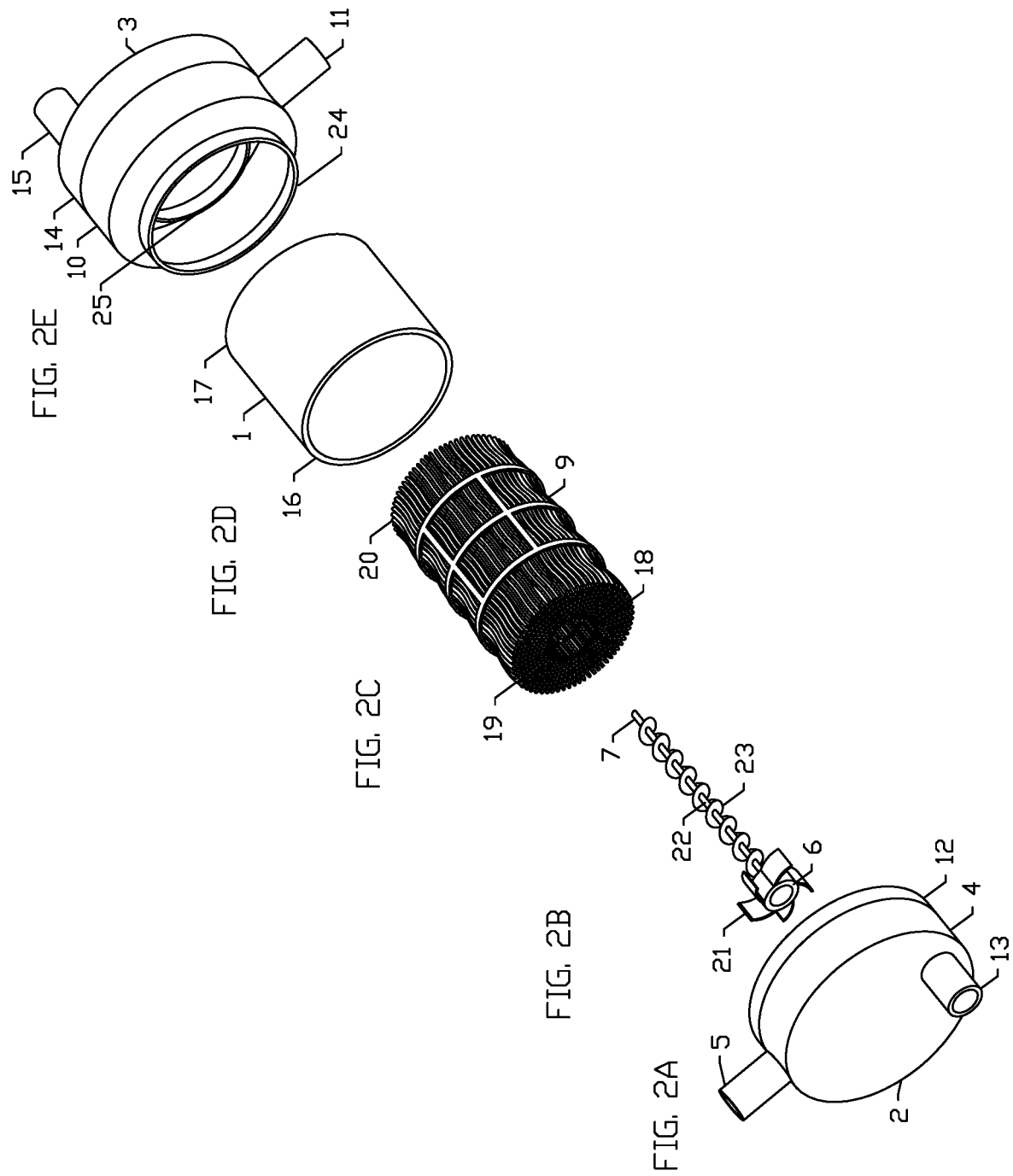

FIG. 3A
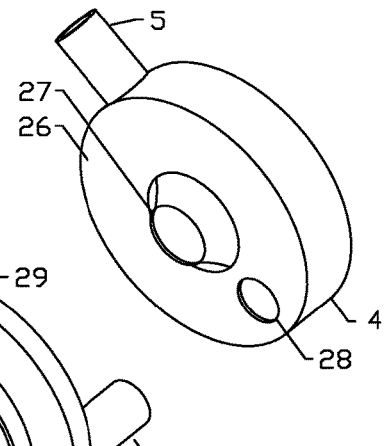
FIG. 3B
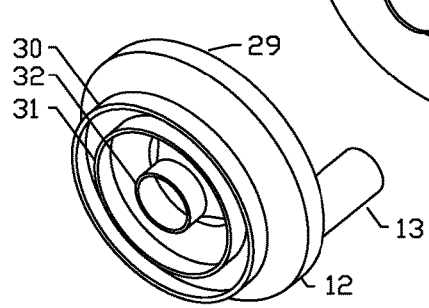
FIG. 3C
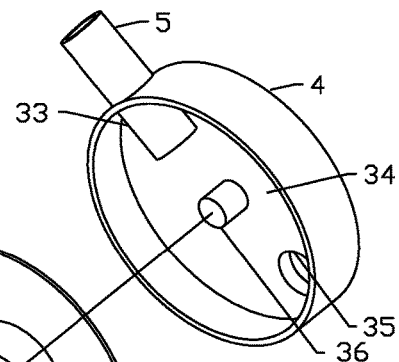
FIG. 3D
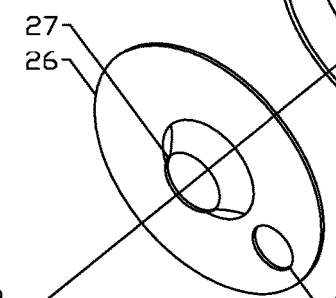
FIG. 3E
FIG. 3F
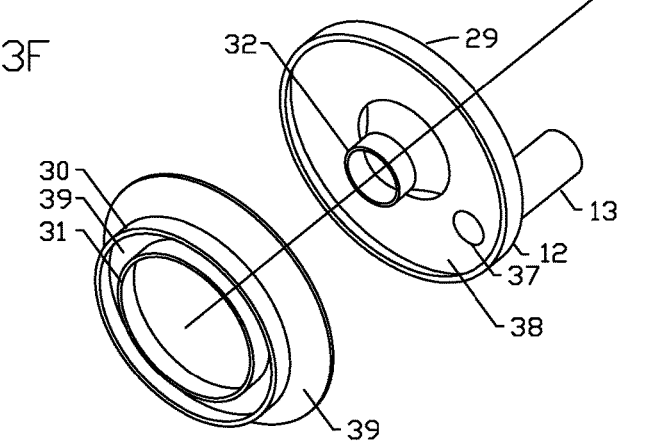

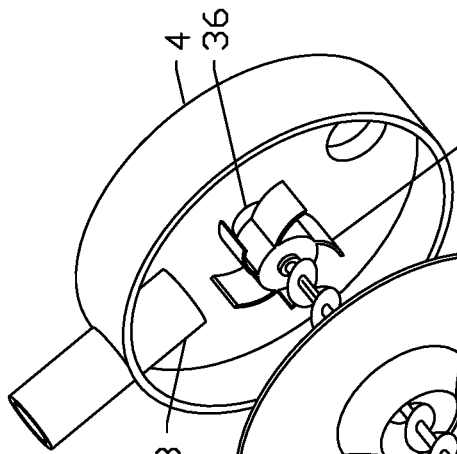
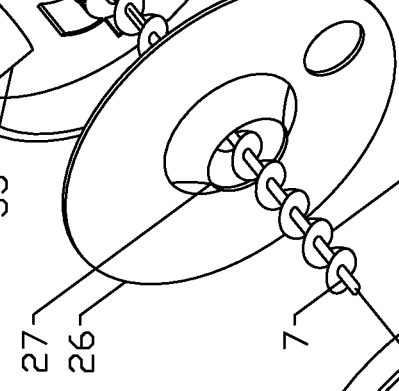
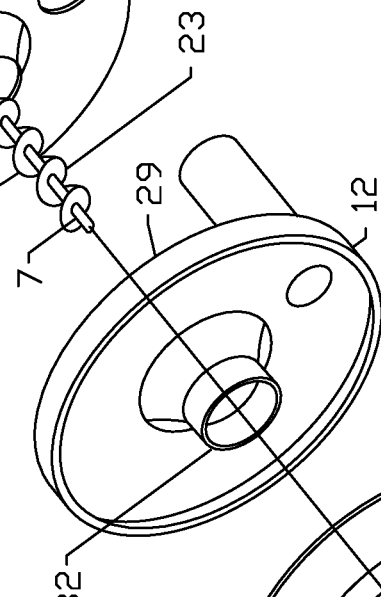
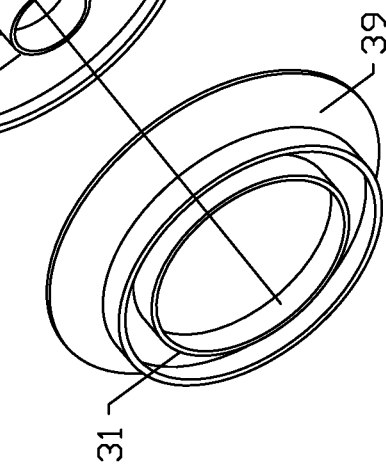

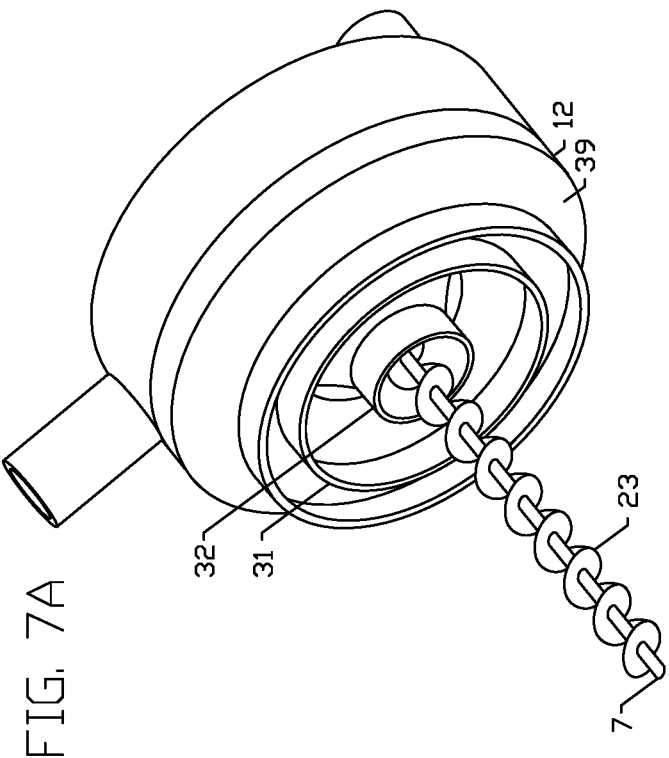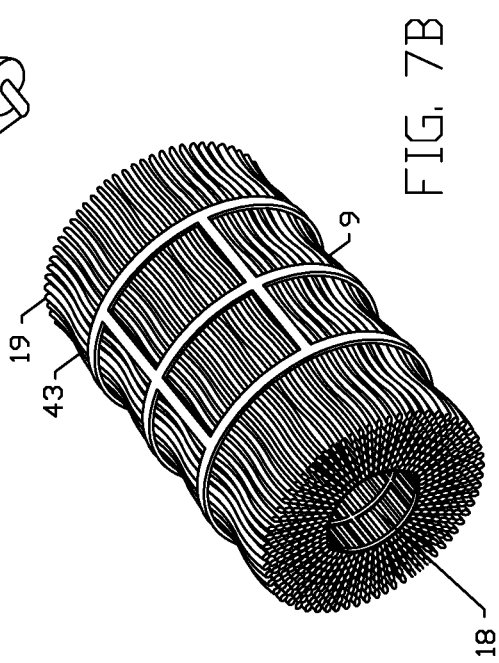

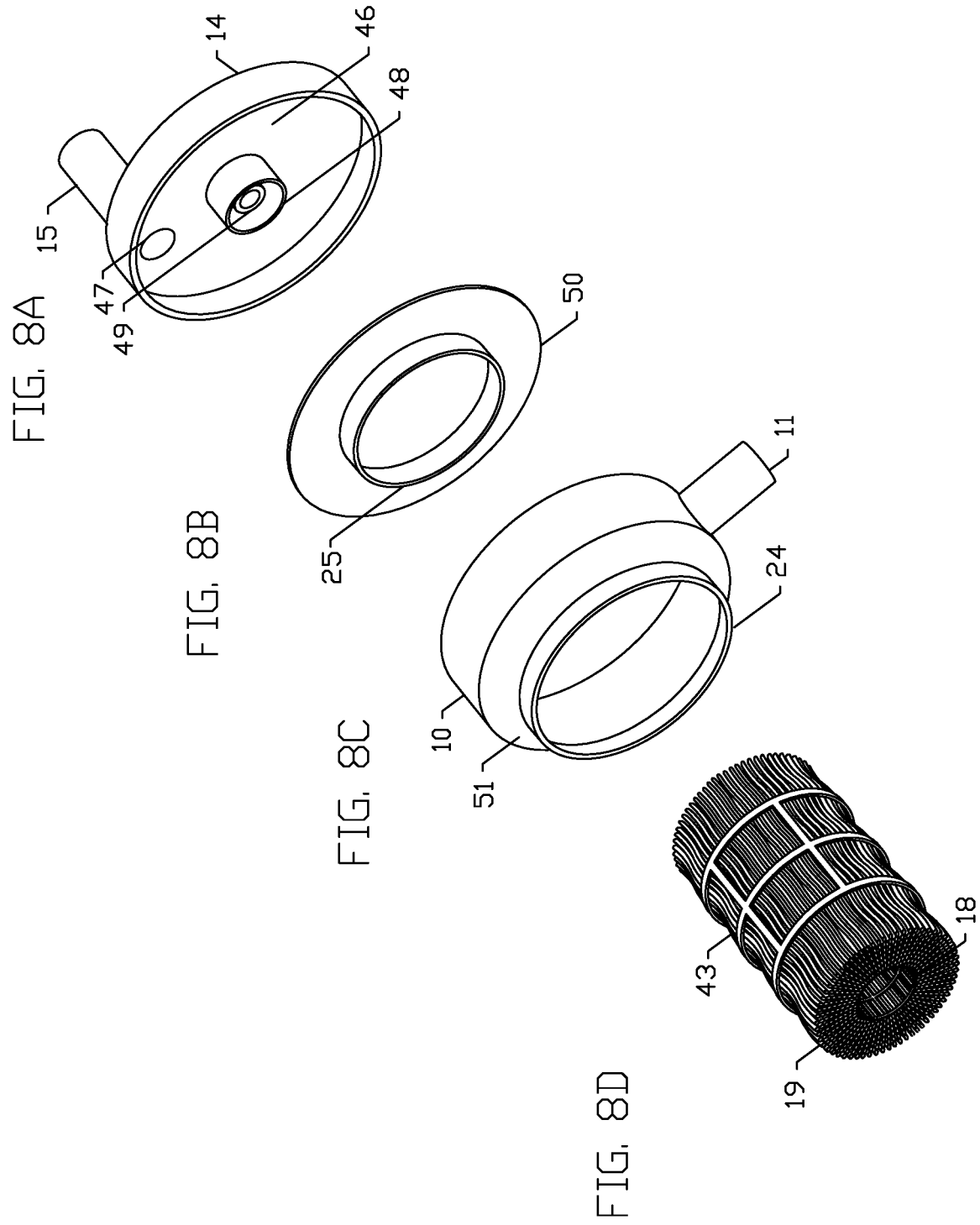

CENTRIFUGAL-DIALYSATE-FLOW HEMODIALIZER

CROSS REFERENCE TO RELATED APPLICATIONS

Attached please refer to the Information Disclosure Statement for the cross reference to related applications.

TECHNICAL FIELD

The present invention relates generally to the field of blood dialyzer. More specifically, the present invention provides a hemodialyzer for clinical hemodialysis for patients in renal failure.

BACKGROUND OF THE INVENTION

Hemodialysis has been successfully implemented to remove metabolic toxins from a patient whose kidney function no longer supports adequate clearance of the metabolic toxins from the patient's body. A critical component of the hemodialysis comprises hemodialyzer which removes the metabolic toxins mostly through diffusion of small molecule solutes and convection of middle molecules across a membrane of the hemodialyzer.

Efficiency of the hemodialyzer is known to depend on diffusive clearance of the small molecule solutes (KoA: mass transfer coefficient Ko×mass transfer area A), convective clearance of the middle molecules (Kuf: volume of fluid transferred across the membrane in mmHg of pressure gradient) and hydrostatic pressure gradient across the membrane of the hemodialyzer (TMP—TransMembrane Pressure). Of these, the diffusive clearance (diffusive mass transfer) appears to be limited by a dialysate phase in a way that the KoA increases proportionally to an increase in a dialysate flow rate but not to an increase in a blood flow rate. In a hemodialyzer system having a constant dialysate flow rate, and a fixed surface area and thickness of dialyzer membrane, the KoA is dependent on a concentration gradient between blood and dialysate, and on distribution of the blood in a blood compartment coaxially flowing in a countercurrent direction to the dialysate in a dialysate compartment. It is well known that the efficiency of the hemodialyzer decreases when there is a mismatch between blood and dialysate flow distributions.

The majority of hemodialyzers in a cylindrical configuration available for clinical use have been found to have non-uniform blood distribution profiles between a central region and a peripheral region of a packed bundle of hollow fibers for a blood phase. Uniformity of blood distribution is inversely affected by concentration of red blood cells in the blood, wherein a higher concentration of the red blood cells in the blood phase is associated with a higher blood flow rate across and a higher wall shear stress on the hollow fibers located centrally than on those located peripherally in the packed bundle of the hollow fibers. For the dialysate phase, dialysate flow distribution and flow rate are affected by presence of irregularities in inter-fiber channels and gaps in a packing structure of the packed bundle of the hollow fibers. The packed bundle of the hollow fibers is more concentrated and more tightly packed in the central region than in the peripheral region of said packed bundle, resulting in a preferential distribution of dialysate flow and a greater dialysate flow rate in the peripheral region than in the central region which may harbor stagnant areas.

Decrease in the efficiency of a cylindrical hemodialyzer due to the non-uniform dialysate flow distribution and the non-uniform dialysate flow rate seen in a configuration of the coaxial countercurrent flow between the blood and the dialysate can be minimized by a specific configuration of the packing structure of the hollow fibers such as Moire structure. It can also be ameliorated by a change in configuration of the dialysate flow from the coaxial countercurrent flow to a centrifugal flow moving radially across the packed bundle of the hollow fibers from the central region to the peripheral region of the packed bundle. In the centrifugal flow configuration of the dialysate flow, the central region having the more densely packed bundle of the hollow fibers receives the dialysate at its highest flow rate which centrifugally decreases across a radius of the packed bundle toward the peripheral region. The central region of the packed bundle which has the highest concentration of the red blood cells in the blood phase receives the dialysate at its highest flow rate centrifugally moving away from an axis of the packed bundle, which exposes the blood phase in the central region to an increase in the dialysate flow rate. As indicated above, a regional KoA of the central region increases by the increase in the flow rate of the centrifugal dialysate flow, thus minimizing effects of the non-uniform blood distribution on the efficiency of the hemodialyzer.

SUMMARY OF THE INVENTION

To improve on the diffusive clearance of the small molecule solutes in a cylindrical hemodialyzer, the present invention of a centrifugal-dialysate-flow hemodialyzer comprises a blood compartment having a packed bundle of hollow fibers in a doughnut configuration on a radial cross-section, and a dialysate compartment having an axial spiral flow converter slidably inserted in a center of the packed bundle of the hollow fibers and an outer circumferential space encircling an outer circumferential layer of the packed bundle of the hollow fibers housed in a cylindrical tube. The axial spiral flow converter comprises a head portion having a rotary propeller coaxially adjoining a stem portion having a longitudinal spiral blade. The rotary propeller is coaxially housed in a dialysate inlet subcompartment which is connected to a dialysate intake tube in a way that the rotary propeller is passively rotatable by an incoming dialysate into the dialysate inlet subcompartment from the dialysate intake tube. The longitudinal spiral blade is slidably inserted in the center of the packed bundle of the hollow fibers in the doughnut configuration for a full length of the packed bundle.

In one embodiment, the cylindrical hemodialyzer comprises a proximal dialyzer compartment, a mid tubular dialyzer compartment, and a distal dialyzer compartment. The proximal dialyzer compartment comprises the dialysate inlet subcompartment distally adjoining a blood outlet subcompartment. The distal dialyzer compartment comprises a distal dialysate outlet subcompartment distally adjoining a blood inlet subcompartment. A proximal portion of the mid tubular dialyzer compartment adjoins a distal portion of the blood outlet subcompartment proximally. A distal portion of the mid tubular dialyzer compartment adjoins a proximal portion of the dialysate outlet subcompartment. Blood flows from the blood inlet subcompartment of the distal dialyzer compartment to the blood outlet subcompartment of the proximal dialyzer compartment. Dialysate flows from the dialysate inlet subcompartment of the proximal dialyzer compartment to the dialysate outlet subcompartment of the distal dialyzer compartment, which establishes a countercurrent flow configuration between dialysate flow and blood flow.

In one embodiment, the dialysate inlet subcompartment and the blood outlet subcompartment are compartmentalized without communication by a radial wall disposed between said dialysate inlet subcompartment and said blood outlet subcompartment. The dialysate inlet subcompartment comprises a first cylindrical space and is provided in a cylindrical tubular configuration having an upper radial wall, a tubular side wall and the radial wall disposed distally. The dialysate intake tube adjoins the dialysate inlet subcompartment and opens to the first cylindrical space of the dialysate inlet subcompartment. Around a center of the radial wall disposed distally, a tubular opening coaxially adjoins the radial wall. The tubular opening is provided in a tubular configuration having a flush proximal end with the radial wall and a tubular cylinder of a length that goes through the blood outlet subcompartment and opens to the proximal portion of the mid tubular dialyzer compartment. The rotary propeller of the axial spiral flow converter is disposed inside the first cylindrical space in a way that the rotary propeller is rotatable about a longitudinal axis of the cylindrical hemodialyzer and that the rotary propeller is rotatably propelled by the incoming dialysate from the dialysate intake tube. A distal portion of the tubular cylinder is configured to be leakproofly inserted in a proximal portion of an open central tubular column of the packed bundle of the hollow fibers in the doughnut configuration housed in the mid tubular dialyzer compartment.

In one embodiment, the blood outlet subcompartment of the proximal dialyzer compartment comprises a second cylindrical space, provided in a cylindrical tubular configuration, having the radial wall of the dialysate inlet subcompartment, a tubular side wall, and a lower radial wall. The radial wall of the dialysate inlet subcompartment serves as an upper wall for the blood outlet subcompartment, and is configured with a hole to accommodate a blood output tube. The blood output tube is provided in a tubular configuration, and fixedly connected to the hole of the radial wall of the dialysate inlet subcompartment. The lower radial wall of the proximal dialyzer compartment comprises a tubular opening coaxially disposed in said lower radial wall. The tubular opening is provided in a tubular configuration having a flush proximal end with the lower radial wall and a tubular cylinder of a length that protrudes into and opens to the proximal portion of the mid tubular dialyzer compartment. A distal portion of the tubular cylinder is configured to leakproofly encase a proximal portion of a circumferential perimeter of the packed bundle of the hollow fibers housed in the mid tubular dialyzer compartment. The tubular opening of the lower radial wall of the proximal dialyzer compartment is much larger in size than the tubular cylinder proximally adjoining the tubular opening of the distally disposed radial wall of the first cylindrical space of the dialysate inlet subcompartment. Size difference in width between the tubular opening of the lower radial wall and the tubular cylinder proximally adjoining the tubular opening of the distally disposed radial wall is configured to be equivalent to a width from an edge of the open central tubular column to the outer circumferential layer of the packed bundle of the hollow fibers. An exposed proximal end of the packed bundle of the hollow fibers leakproofly encased by the distal portion of the tubular cylinder of the blood outlet subcompartment is open to the second cylindrical space of the blood outlet subcompartment, having a flush configuration with an inner surface of with the lower radial wall of the blood outlet subcompartment. The second cylindrical space of the blood outlet subcompartment collects the blood from a proximal end of the packed bundle of the hollow fibers, and transmits out the blood through the blood output tube.

In one embodiment, the mid tubular dialyzer compartment comprises a cylindrical tube having the proximal portion, the distal portion and a mid portion connecting the proximal portion to the distal portion. The proximal portion of the mid tubular dialyzer compartment fixedly and leakproofly adjoins the distal portion of the blood outlet subcompartment under the lower radial wall of the proximal dialyzer compartment. The distal portion of the mid tubular dialyzer compartment fixedly and leakproofly adjoins and opens without an intervening wall to the proximal portion of the dialysate outlet subcompartment of the distal dialyzer compartment. The mid tubular dialyzer compartment coaxially encloses the packed bundle of the hollow fibers in a way that there is provided the outer circumferential space bordered by the outer circumferential layer of the packed bundle of the hollow fibers and the inner surface of said mid tubular dialyzer compartment. The outer circumferential layer of the packed bundle of the hollow fibers is separated by >1 mm from the inner surface of said mid tubular dialyzer compartment. The dialysate radially flows from the open central tubular column of the packed bundle of the hollow fibers to the outer circumferential space in a centrifugal direction.

In one embodiment, the dialysate outlet subcompartment and the blood inlet subcompartment of the distal dialyzer compartment are compartmentalized without communication by an upper radial wall disposed between said dialysate outlet subcompartment and said blood inlet subcompartment. The dialysate outlet subcompartment comprises a third cylindrical space, provided in a cylindrical tubular configuration, having a tubular side wall and the upper radial wall, but does not have a wall between the third cylindrical space and the mid tubular dialyzer compartment. A dialysate output tube is fixedly attached to a hole made on the tubular side wall and opens to the third cylindrical space. The upper radial wall of the dialysate outlet subcompartment comprises a tubular opening coaxially adjoining the upper radial wall. The tubular opening is provided in a tubular configuration having a flush distal end with the upper radial wall, and adjoins a tubular cylinder of a length that protrudes into and opens to the distal portion of the mid tubular dialyzer compartment. A proximal portion of the tubular cylinder is configured to leakproofly encase the distal portion of the circumferential perimeter of the packed bundle of the hollow fibers housed in the mid tubular dialyzer compartment. The distal portion of the packed bundle of the hollow fibers coaxially goes through the dialysate outlet subcompartment, which produces a doughnut configuration of the third cylindrical space.

In one embodiment, the blood inlet subcompartment of the distal dialyzer compartment comprises a fourth cylindrical space, provided in a cylindrical tubular configuration, having the upper radial wall of the dialysate outlet subcompartment, a tubular side wall, and a lower radial wall. A tubular cylinder coaxially and fixedly adjoins an upper surface of the lower radial wall around a center of said upper surface of the lower radial wall. The tubular cylinder runs for a length that goes through the dialysate outlet subcompartment and opens to the distal portion of the mid tubular dialyzer compartment. A proximal portion of the tubular cylinder is configured to be leakproofly inserted in a distal portion of the open central tubular column of the packed bundle of the hollow fibers in the doughnut configuration housed in the mid tubular dialyzer compartment. Disposed inside the tubular cylinder of the blood inlet subcompartment, an anchoring flange, provided in a configuration of tubular cylinder, coaxially and fixedly adjoins the upper surface of the lower radial wall around the center of said upper surface of the lower radial wall. A distal tip of the longitudinal spiral blade of the axial spiral flow converter is rotatably housed in a tubular cylinder of the anchoring flange. The lower radial wall of the blood inlet subcompartment is configured with a hole to accommodate a blood intake tube. The blood intake tube is provided in a tubular configuration, and fixedly connected to the hole of the lower radial wall of the blood inlet subcompartment. An exposed distal end of the packed bundle of the hollow fibers leakproofly encased by the proximal portion of the tubular cylinder of the dialysate outlet subcompartment is open to the fourth cylindrical space of the blood inlet subcompartment, having a flush configuration with an inner surface of the upper radial wall of the dialysate outlet subcompartment. The blood is pushed into the fourth cylindrical space through the blood intake tube, following which the blood goes through individual hollow fibers of the packed bundle of the hollow fibers from the distal portion to the proximal portion of the said packed bundle of the hollow fibers into the blood outlet subcompartment of the proximal dialyzer compartment. It then goes out through the blood output tube.

In one embodiment, the axial spiral flow converter comprises the head portion having the rotary propeller fixedly adjoining the stem portion of the longitudinal spiral blade along a longitudinal axis of the axial spiral flow converter. The rotary propeller comprises a set of rotary blades fixedly attached to a rotary shaft at an angle ranging from 0° to 180° degree. The rotary propeller is rotatably housed in the first cylindrical space of the dialysate inlet subcompartment in a way that the rotary propeller is rotatable about the longitudinal axis of the cylindrical hemodialyzer and that the rotary propeller is rotatably propelled by the incoming dialysate from the dialysate intake tube into the first cylindrical space. The longitudinal spiral blade comprises a longitudinal shaft to which a single helical blade fixedly encircles said longitudinal shaft from a bottom of the rotary propeller to the distal tip portion of the longitudinal spiral blade. The longitudinal spiral blade is slidably and coaxially placed in the tubular cylinder of the dialysate inlet subcompartment, in the open central tubular column of the packed bundle of the hollow fibers for its entire length, and in the tubular cylinder of the blood inlet subcompartment. The distal tip of the longitudinal spiral blade is rotatably housed in the tubular cylinder of the anchoring flange of blood inlet subcompartment. The longitudinal spiral blade in a rotating configuration pulls the dialysate in the open central tubular column and centrifugally spreads the dialysate in the open central tubular column across the packed bundle of the hollow fibers to the outer circumferential space bordered by the outer circumferential layer of the packed bundle of the hollow fibers.

In one embodiment, the packed bundle of the hollow fibers contains about 10,000 hollow fibers, with an inner diameter of each wet fiber measuring about 200 micrometer, a membrane thickness measuring about 20-45 micrometer, and a length measuring 80-240 mm. The hollow fibers are made of any of following polymers: Cuprophan, Cellulose diacetate, Cuproammonium rayon, Hemophan, Polysulfone, Polycarbonate, Cellulose triacetate, Polyamide, Polyethersulfone, Polyacrilonitrile, or Polymethylmethacrylate. An individual hollow fiber is configured to be elastomerically stretchable upon a dialysate flow tangentially contacting the individual hollow fiber, so as to impart longitudinal flexibility.

In one embodiment, the packed bundle of the hollow fibers is provided in the doughnut configuration on a radial cross-section having an empty column of the open central tubular column circumferentially surrounded by a plurality of the hollow fibers packed in a cylindrical configuration. A first set of resiliently stiff string harness in a tubular configuration is insertably placed inside the open central tubular column so as to provide said open central tubular column with a structural strength. A second set of elastomeric string harness in a tubular configuration is provided on an outer part of the outer circumferential layer of the packed bundle of the hollow fibers to tie up said packed bundle of the hollow fibers. The elastomeric string harness is made of an elastomeric polymer, and is configured to be reversibly and circumferentially stretchable so as to let individual hollow fibers radially pushed apart from other adjacent individual hollow fibers by an outward pressure of the centrifugal dialysate flow radially moving from the open central tubular column to the peripheral layer of the packed bundle of the hollow fibers. The elastomeric string harness in a stretched configuration allows the individual hollow fibers of the packed bundle of the hollow fibers to be radially dispersed in a way that there is an increase in an interfibrillar space between two adjacent individual hollow fibers by the outward pressure of the centrifugal dialysate flow from the open central tubular column to the peripheral layer of the packed bundle of the hollow fibers. The space permits the dialysate to flow through the interfibrillar space in a centrifugal direction. The packed bundle of the hollow fibers is coaxially placed inside the mid tubular dialyzer compartment, wherein the proximal portion of the circumferential perimeter of the packed bundle of the hollow fibers housed in the mid tubular dialyzer compartment is leakproofly encased by the distal portion of the tubular cylinder of the blood outlet subcompartment, and wherein the distal portion of the circumferential perimeter of said packed bundle of the hollow fibers is leakproofly encased by the proximal portion of the tubular cylinder of the dialysate outlet subcompartment.

In one embodiment, the dialysate flows into the first cylindrical space of the dialysate inlet subcompartment through the dialysate intake tube, and rotates the rotary propeller of the axial spiral flow converter. The rotary propeller coaxially rotates the longitudinal spiral blade which then centrifugally converts an axial flow of the dialysate coming into the open central tubular column of the packed bundle of the hollow fibers to a radial flow toward the outer circumferential space bordered by the outer circumferential layer of the packed bundle of the hollow fibers and an inner surface of the mid tubular dialyzer compartment. The dialysate collected in the outer circumferential space then flows to the third cylindrical space of the dialysate outlet subcompartment of the distal dialyzer compartment. The dialysate collected in the third cylindrical space of the dialysate outlet subcompartment from the outer circumferential space of the mid tubular dialyzer compartment then flows out through the dialysate output tube.

BRIEF DESCRIPTION OF THE DRAWINGS

FIGS. 2A-2E represent a schematic exploded three-dimensional view of individual components of the centrifugal-dialysate-flow hemodialyzer.

FIGS. 3A-3F illustrate a schematic exploded three-dimensional view of individual components of a dialyzer inlet compartment.

FIGS. 5A-5D show a schematic illustration of an in-situ placement of the axial spiral flow converter inside the dialyzer inlet compartment.

FIGS. 7A-7B show a schematic view of a configuration of combination of the dialyzer inlet compartment having the axial spiral in place with the packed bundle of the hollow fibers.

FIGS. 8A-8D show a schematic illustration of individual components of a dialyzer outlet compartment and the packed bundle of the hollow fibers.

DETAILED DESCRIPTION OF THE DRAWINGS

As described below, the present invention provides a centrifugal-dialysate-flow hemodialyzer comprising a blood compartment having a packed bundle of hollow fibers in a doughnut configuration on a radial cross-section, and a dialysate compartment having an axial spiral flow converter slidably inserted in a center of the packed bundle of the hollow fibers and an outer circumferential space encircling an outer circumferential layer of the packed bundle of the hollow fibers housed in a cylindrical tube. It is to be understood that the descriptions are solely for the purposes of illustrating the present invention, and should not be understood in any way as restrictive or limited. Embodiments of the present invention are preferably depicted with reference to FIGS. 1 to 12, however, such reference is not intended to limit the present invention in any manner. The drawings do not represent actual dimension of devices, but illustrate the principles of the present invention.

Figure 1:
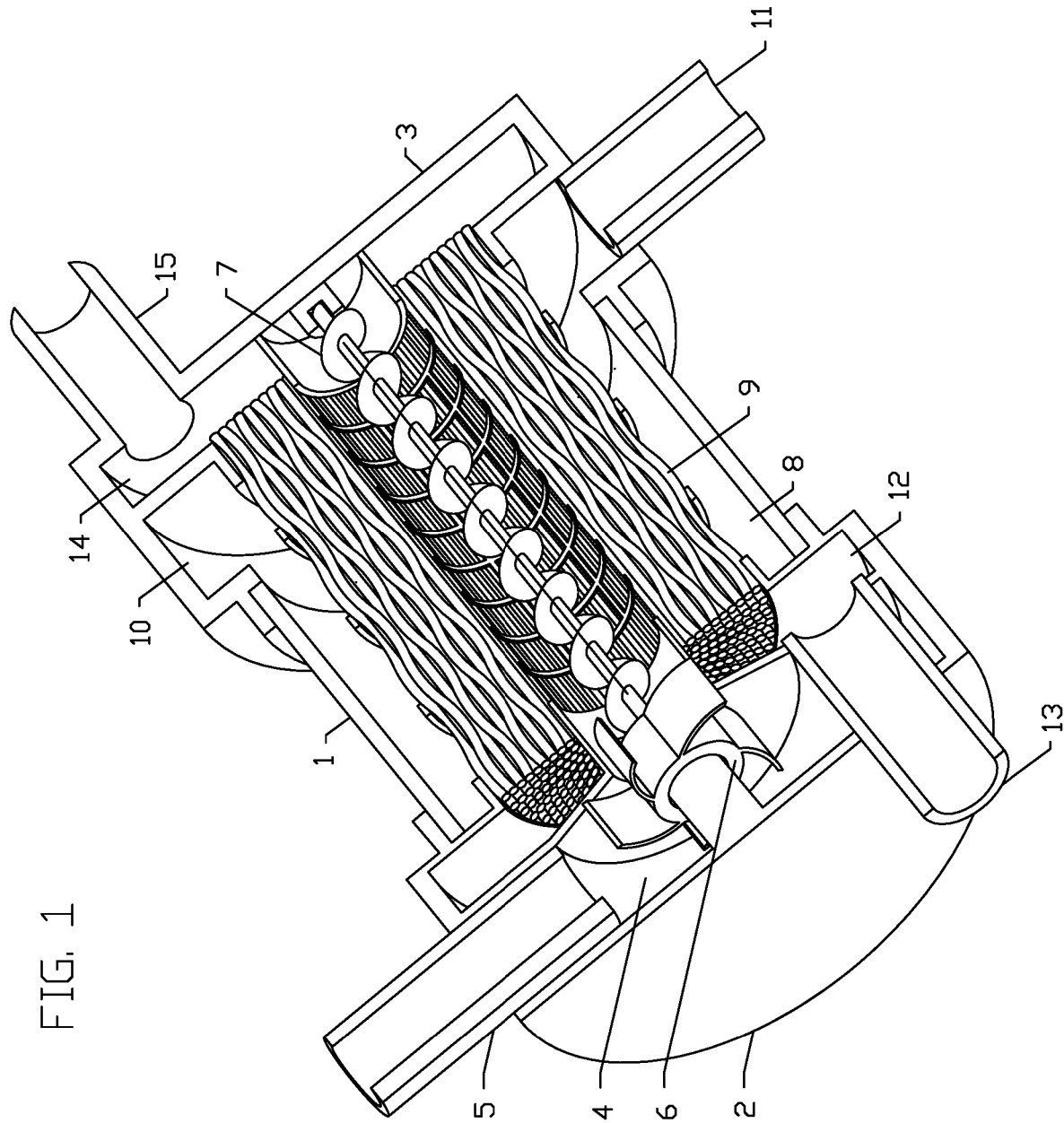
FIG. 1 shows a schematic three-dimensional exposed cut-out view of a centrifugal-dialysate-flow hemodialyzer.

FIG. 1 shows a schematic three-dimensional exposed cut-out view of the centrifugal-dialysate-flow hemodialyzer. The centrifugal-dialysate-flow hemodialyzer is provided in a cylindrical configuration, which comprises a proximal dialyzer compartment 2, a mid tubular dialyzer compartment 1, and a dialyzer compartment 3. The proximal dialyzer compartment 2 comprises a dialysate inlet subcompartment 4 distally adjoining a blood outlet subcompartment 12. The dialyzer compartment 3 comprises a dialysate outlet subcompartment 10 distally adjoining a blood inlet subcompartment 14. A proximal portion of the mid tubular dialyzer compartment 1 adjoins a distal portion of the blood outlet subcompartment 12 proximally. A distal portion of the mid tubular dialyzer 1 compartment adjoins a proximal portion of the dialysate outlet subcompartment 10. Dialysate delivered via a dialysate intake tube 5 into the dialysate inlet subcompartment 4 rotates a rotary propeller 6 of an axial spiral flow converter which in turn rotates a longitudinal spiral blade 7. The rotary propeller 6 and the longitudinal spiral blade 7 propel the dialysate in an open central tubular column of a packed bundle of hollow fibers 9 centrifugally to an outer circumferential space 8, in a direction from the dialysate inlet subcompartment 4 of the proximal dialyzer compartment 2 to the dialysate outlet subcompartment 10 of the dialyzer compartment 3. The dialysate then flows out from the dialysate outlet subcompartment 10 via a dialysate output tube 11. Blood delivered via a blood intake tube 15 into the blood inlet subcompartment 14 of the dialyzer compartment 3 moves through the packed bundle of the hollow fibers 9 to the blood outlet subcompartment 12 of the proximal dialyzer compartment 2. The blood then flows out via a blood output tube 13. Thus, a countercurrent flow configuration is established between the dialysate flow and the blood flow.

FIGS. 2A-2E represent a schematic exploded three-dimensional view of individual components of the centrifugal-dialysate-flow hemodialyzer. FIG. 2A shows the proximal dialyzer compartment 2 comprising the dialysate inlet subcompartment 4 axially adjoining the blood outlet subcompartment 12. Referring to FIG. 1, the dialysate intake tube 5 adjoins and opens to the dialysate inlet subcompartment 4, and the blood output tube 13 adjoins and opens to the blood outlet subcompartment 12, and protrudes out through the dialysate inlet subcompartment 4. The axial spiral flow converter shown in FIG. 2B comprises the rotary propeller 6 having a plurality of spiral blades 21 arranged in parallel to a longitudinal axis of said axial spiral flow converter, and the longitudinal spiral blade 7 having a single helical blade 23 helically and fixedly encircling a longitudinal stem 22. The packed bundle of the hollow fibers 9 shown in FIG. 2C comprises the open central tubular column 18 and an outer circumferential layer 19 of the hollow fibers 20. The longitudinal spiral blade 7 is slidably and coaxially inserted into the open central tubular column 18 of the packed bundle of the hollow fibers 9. The mid tubular dialyzer compartment 1 is provided in an open tubular configuration having a proximal portion 16 and a distal portion 17. Referring to FIG. 1, the proximal portion 16 is fixedly encircled by a circular flange (not shown) disposed at an open distal portion (not shown) of the blood outlet subcompartment 12, and the distal portion 16 is fixedly encircled by a circular flange 24 of a proximal tubular portion of the dialysate outlet subcompartment 10. FIG. 2E shows the dialyzer compartment 3 comprising the dialysate outlet subcompartment 10 axially adjoining the blood inlet subcompartment 14. The proximal tubular portion of the dialysate outlet subcompartment 10 comprises a wide tubular opening encircled by the circular flange 24. Referring to FIG. 1, the dialysate output tube 11 adjoins and opens to the dialysate outlet subcompartment 10, and the blood intake tube 15 adjoins and opens to the blood inlet subcompartment 14. A proximal tubular portion of the blood inlet subcompartment 14 comprises a tubular opening encircled by a circular flange 25. The circular flange 25 is configured to fixedly encircle a distal portion of the packed bundle of the hollow fibers 9.

FIGS. 3A-3F illustrate a schematic exploded three-dimensional illustration of individual components of the proximal dialyzer compartment 2, viewed from bottom up. FIG. 3A shows a lower radial wall 26 of the dialysate inlet subcompartment 4 having the dialysate intake tube 5 open to said dialysate inlet subcompartment 4. A tubular rim 27 in a conical configuration having a tubular opening is disposed around a center of the distal radial wall 26. A hole 28 is provided on a peripheral region of the lower radial wall 26, which is configured to let the blood output tube 13 leakproofly penetrate through said hole 28. FIG. 3B shows an outer circular flange 30 and an inner circular flange 31 protruding from a lower radial wall of the blood outlet subcompartment 12. An upper radial wall 29 covers an upper part of the blood outlet subcompartment 12. The blood output tube 13 protrudes from the upper radial wall 29 and opens to the blood outlet subcompartment 12. Shown in FIG. 3C, the dialysate inlet subcompartment 4 further comprises an upper radial wall 34 and an axial pin 36 fixedly adjoining a center of an undersurface of the upper radial wall 34. In this particular view, a longitudinal axis of the dialysate intake tube 5 having an inner portion 33 inside the dialysate inlet subcompartment 4 is fixedly inserted at a right angle to a longitudinal axis of the proximal dialyzer compartment 2. Referring to FIG. 2B, the axial pin 36 is configured to be slidably inserted into a central tubular cylinder of the rotary propeller 6 which rotates about said axial pin 36. A hole 35 is provided on a peripheral region of the upper radial wall 34, which is configured to let the blood output tube 13 leakproofly penetrate through said hole 35. The hole 35 is longitudinally aligned with the hole 28 shown in FIG. 3D. Shown in FIG. 3E, the blood outlet subcompartment 12 comprises the upper radial wall 29, a proximal inner coaxial tubular cylinder 32 protrudably adjoining an undersurface 38 of the upper radial wall 29, and an circular opening 37 of the blood output tube 13. The proximal inner coaxial tubular cylinder 32 concentrically divides the blood outlet subcompartment 12 into an outer tubular columnar space and an inner tubular columnar space. Blood only resides in the outer tubular columnar space. The inner tubular columnar space is only filled in with dialysate. Referring to FIG. 2C, the proximal inner coaxial tubular cylinder 32 is configured to be fixedly inserted into a proximal portion of the open central tubular column 18 of the packed bundle of the hollow fibers 9. FIG. 3F shows the lower radial wall 39 having the outer circular flange 30 encircling the inner circular flange 31 which is smaller than the outer circular flange 30. Both the outer and inner circular flanges are coaxially aligned and fixedly attached to an undersurface of the lower radial wall 39. Referring to FIG. 1, the inner circular flange 31 is fixedly encircling the proximal portion of the packed bundle of the hollow fibers 9. Referring to FIG. 2D, the outer circular flange 30 is fixedly encircling the proximal portion 16 of the mid tubular dialyzer compartment 1.

Figure 4A:
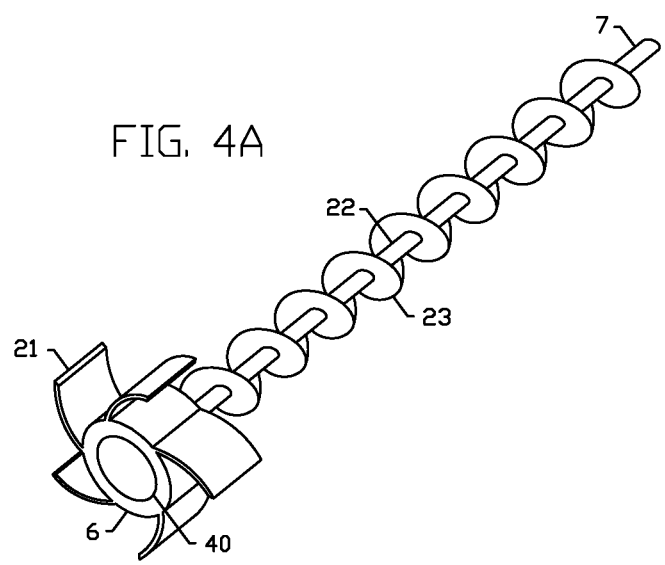
FIGS. 4A-4C depict a schematic view of an axial spiral flow converter.
Figure 4B:
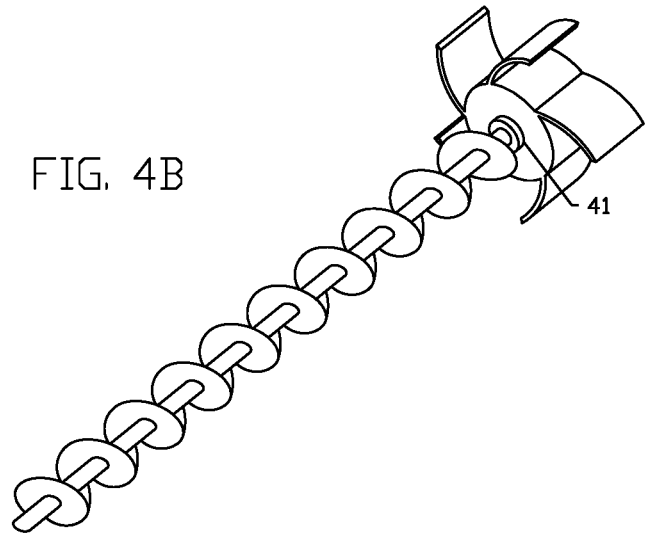
Figure 4C:
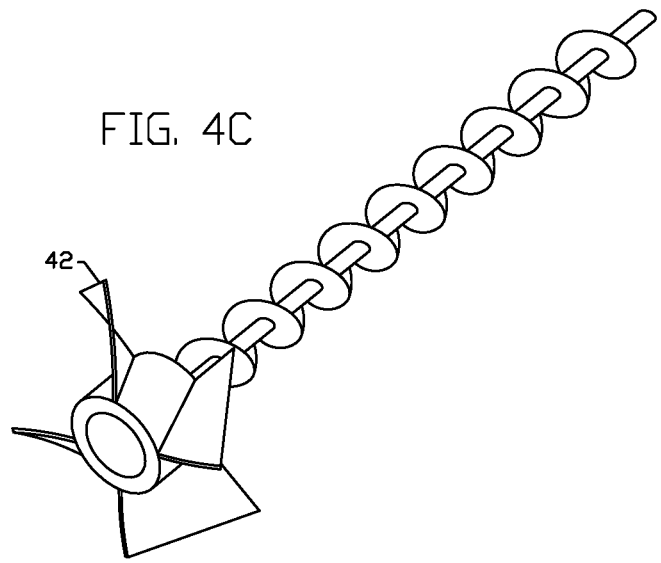
Figure 6A:
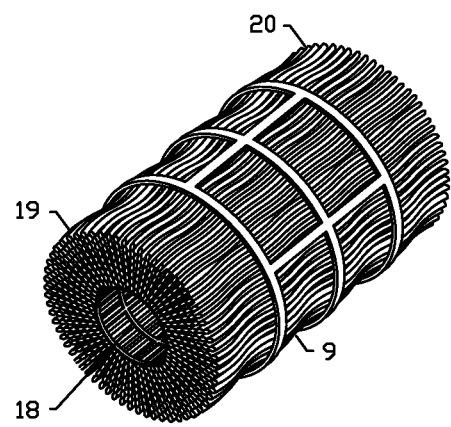
FIGS. 6A-6D show a schematic view of individual components of a packed bundle of hollow fibers.
Figure 6B:
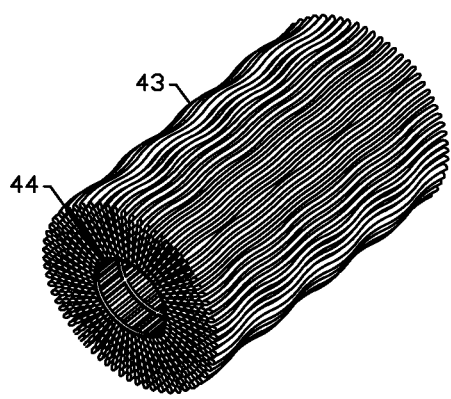
Figure 6C:
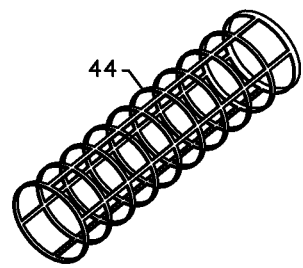
Figure 6D:
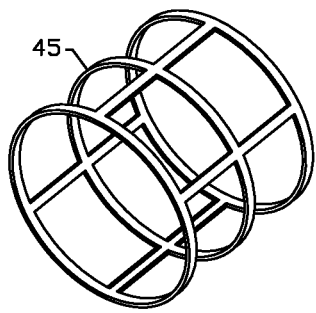

FIG. 4A shows a schematic view of the axial spiral flow converter comprising the rotary propeller 6 as a head portion of said axial spiral flow converter having the open tubular cylinder 40 which is configured to slidably encircle the axial pin 36 shown in FIG. 3C. The plurality of the spiral blades 21 are arranged in parallel to the longitudinal axis of said axial spiral flow converter. The longitudinal spiral blade 7 as a stem portion of said axial spiral flow converter comprises the single helical blade 23 helically and fixedly encircling the longitudinal stem 22. Referring to FIG. 1, the distal portion of the longitudinal spiral blade 7 is slidably and axially inserted in a tubular flange disposed at a center of an undersurface of the lower radial wall of the dialyzer compartment 3. A junction between the rotary propeller 6 and the longitudinal spiral blade is strengthened by a flange 41, shown in FIG. 4B. In another embodiment, the spiral blades of the rotary propeller are configured as helical spiral 42, shown in FIG. 4C. Referring to FIGS. 1 and 3C, the spiral blades 21 arranged in parallel to the longitudinal axis of said axial spiral flow converter are suited for propelling the rotary propeller in a configuration of the longitudinal axis of the dialysate intake tube 5 installed at a right angle to the longitudinal axis of the axial spiral flow converter. The helical spiral 42 is suited for propelling the rotary propeller in a configuration of the longitudinal axis of the dialysate intake tube 5 installed in parallel with or coaxially with the longitudinal axis of the axial spiral flow converter.

FIG. 5A shows the inner portion 33 of the dialysate intake tube placed leveled with and at a right angle with the rotary propeller blades 21 which is rotatably fastened to the axial pin 36. Shown in FIG. 5B, the longitudinal spiral blade 7 with the single helical blade 23 is slidably and coaxially inserted through the tubular rim 27 disposed around the center of the distal radial wall 26 of the dialysate inlet subcompartment 4. The longitudinal spiral blade 7 of the stem portion of the axial spiral flow converter slidably and coaxially goes through the proximal inner coaxial tubular cylinder 32 of the upper radial wall 29 of the blood outlet subcompartment 12, and the inner circular flange 31 of the lower radial wall 39 of the blood outlet subcompartment 12, shown in FIGS. 5C and 5D.

FIGS. 6A-6D show the packed bundle of hollow fibers 9 comprising the individual hollow fibers 20 concentrically stacked up from around a first set of resiliently stiff inner string harness 44 abuttingly disposed on a perimeter of the open central tubular column 18 up to an outer surface 43 of said packed bundle of hollow fibers 9, thus forming a cylindrical tube in a doughnut configuration. The first set of the resiliently stiff inner string harness 44 in a tubular configuration provides said open central tubular column 18 with a structural strength so as to avoid inward collapse of the open central tubular column. A second set of elastomeric outer string harness 45 in a tubular configuration is provided on the outer surface 43 of the outer circumferential layer 19 of the packed bundle of the hollow fibers 9 to securely tie up said packed bundle of the hollow fibers.

FIGS. 7A-7B show a schematic view of an assembly of the proximal dialyzer compartment having the axial spiral in place with the packed bundle of the hollow fibers 9. The inner circular flange 31 protruding from the lower radial wall 39 of the blood outlet subcompartment 12 is configured to fixedly encircle the outer surface 43 of the outer circumferential layer 19 of the proximal portion of the packed bundle of the hollow fibers 9. Referring to FIG. 5C, the proximal inner coaxial tubular cylinder 32 protrudably adjoining the upper radial wall 29 of the blood outlet subcompartment 12 is configured to be fixedly inserted into the proximal portion of the open central tubular column 18 of the packed bundle of the hollow fibers 9. The longitudinal spiral blade 7 having the single helical blade 23 is configured to be slidably and coaxially placed in the open central tubular column 18.

FIG. 8A shows a schematic illustration of the blood inlet subcompartment 14 comprising the blood intake tube 15 with an opening 47 through a lower radial wall 46 into said blood inlet subcompartment 14. A distal inner coaxial tubular cylinder 48 is fixedly and coaxially adjoining an undersurface of the lower radial wall 46, and is configured to be fixedly inserted into the distal portion of the open central tubular column 18 of the packed bundle of the hollow fibers 9 shown in FIG. 8D. The distal inner coaxial tubular cylinder 48 concentrically divides the blood inlet subcompartment 14 into an outer tubular columnar space and an inner tubular columnar space. Blood only resides in the outer tubular columnar space. The inner tubular columnar space is only filled in with dialysate. Referring to FIGS. 1 and 4A, a tubular flange 49 is disposed at a center of an undersurface of the lower radial wall 46 of the blood inlet subcompartment 14, and is configured to slidably and axially encircle the distal portion of the longitudinal spiral blade 7. FIG. 8B shows an upper radial wall 50 configured to divide the dialyzer compartment into the blood inlet subcompartment 14 of FIG. 8A and the dialysate outlet subcompartment 10 of FIG. 8C. The circular flange 25 with a tubular opening proximally and coaxially protrudes from the upper radial wall 50, and is configured to fixedly encircle the outer surface 43 of the outer circumferential layer 19 of the distal portion of the packed bundle of the hollow fibers 9 of FIG. 8D. Shown in FIG. 8C, the dialysate outlet subcompartment 10 comprises the dialysate output tube 11, and the circular flange 24 with the wide tubular opening proximally and coaxially protrudes from a base radial wall 51. The circular flange 24 is configured to fixedly encircle the distal portion 17 of the mid tubular dialyzer compartment 1.

Figure 9:
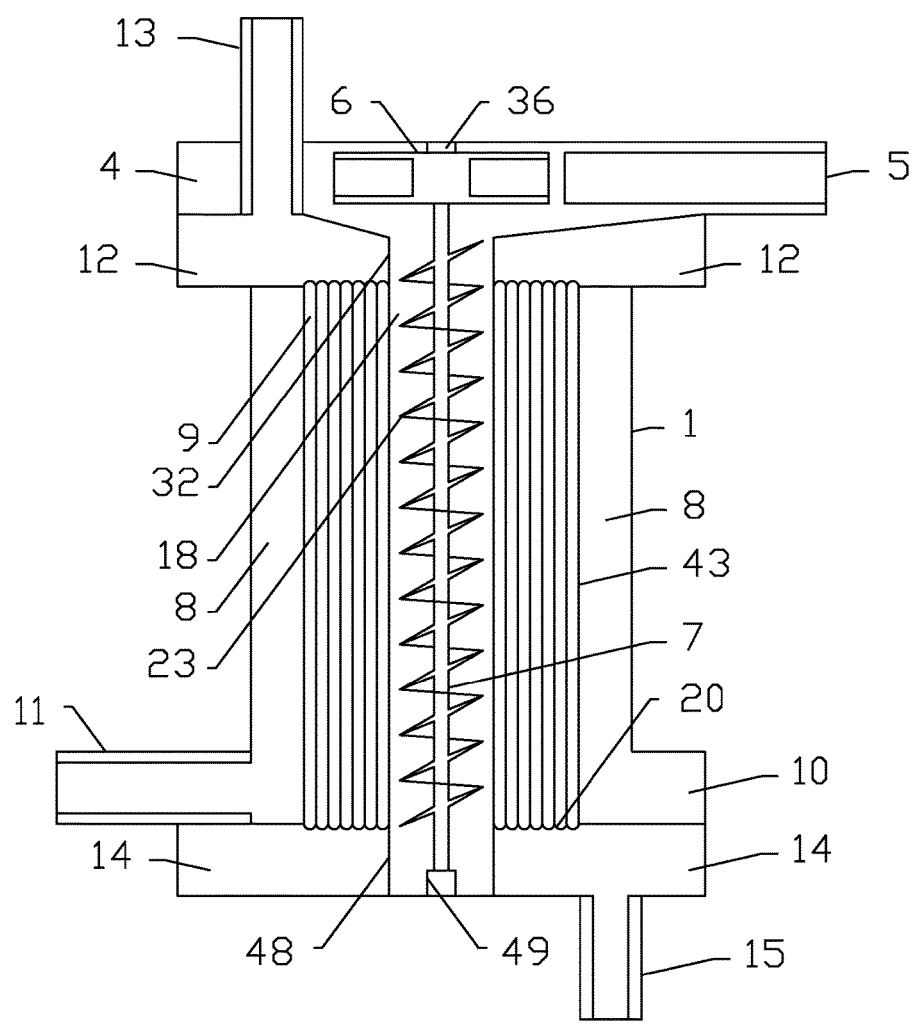
FIG. 9 depicts a two-dimensional view of the individual components of the centrifugal-dialysate-flow hemodialyzer.

FIG. 9 depicts a two-dimensional view of the individual components of the centrifugal-dialysate-flow hemodialyzer. Blood flows from the blood intake tube 15 into the blood inlet subcompartment 14, which then goes through the individual hollow fibers 20 of the packed bundle of the hollow fibers 9 disposed inside the mid tubular dialyzer compartment 1 to the blood outlet subcompartment 12. It then flows out through the blood output tube 13. Therefore, the centrifugal-dialysate-flow hemodialyzer has a blood compartment comprising the blood intake tube 15, the blood inlet subcompartment 14, the packed bundle of the hollow fibers 9, the blood outlet subcompartment 12, and the blood output tube 13. Dialysate flows from the dialysate intake tube 5 into the dialysate inlet subcompartment 4, which then goes through the open central tubular column 18 of the packed bundle of the hollow fibers 9. The dialysate then is centrifugally spread to the outer circumferential space 8 by the single helical blade 23 of the axial spiral flow converter rotated by the rotary propeller 6. The outer circumferential space 8 is provided between the outer surface 43 of the packed bundle of the hollow fibers 9 and the mid tubular dialyzer compartment 1. The rotary propeller 6 is rotatably propelled by an incoming dialysate from the dialysate intake tube 5. The dialysate in the outer circumferential space 8 is collected in the dialysate outlet subcompartment 10 from which the dialysate flows out through the dialysate output tube 11. A dialysate compartment of the centrifugal-dialysate-flow hemodialyzer therefore comprises the dialysate intake tube 5, the dialysate inlet dialysate inlet subcompartment 4, the open central tubular column 18 of the packed bundle of the hollow fibers 9 sealably connected to the dialysate inlet subcompartment 4 by the proximal inner coaxial tubular cylinder 32, the outer circumferential space 8 provided between the outer surface 43 of the packed bundle of the hollow fibers 9 and the mid tubular dialyzer compartment 1, the dialysate outlet subcompartment 10 which is sealably connected to the open central tubular column 18 by the distal inner coaxial tubular cylinder 48, and the dialysate output tube 11. The blood compartment and the dialysate compartment are separated and not directly communicated with each other except through a membrane of the hollow fibers 20 of the packed bundle of the hollow fibers 9. The rotary propeller 6 is stabilized by the axial pin 36, and the longitudinal spiral blade 7 is stabilized by the tubular flange 49.

Figure 10A:
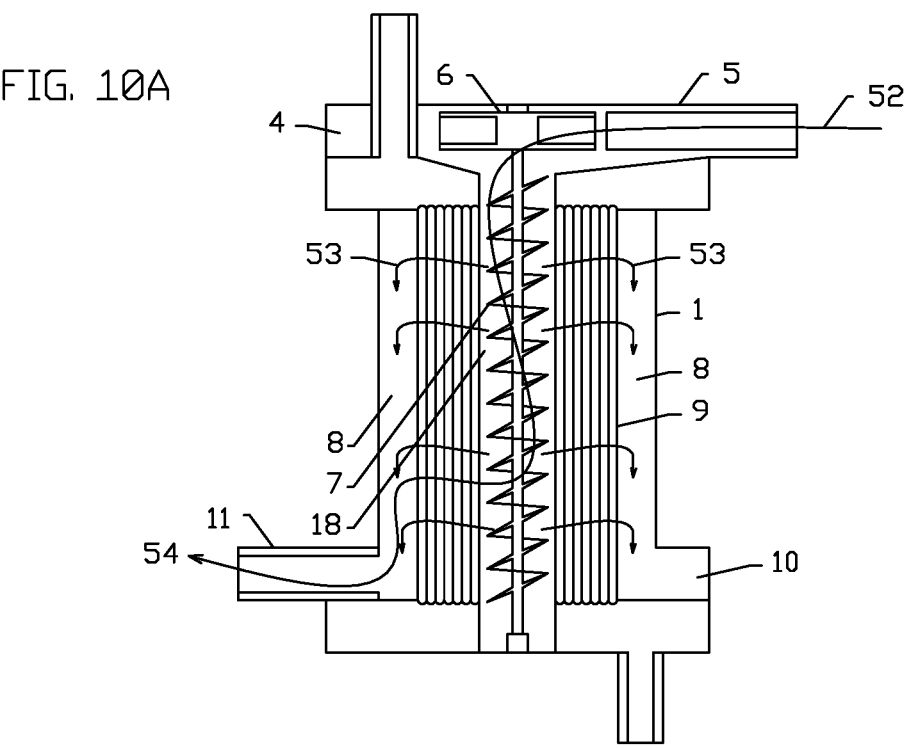
FIGS. 10A-10B show schematic views of centrifugal dialysate flow and blood flow which runs in a countercurrent direction relative to a direction of the centrifugal dialysate flow.
Figure 10B:
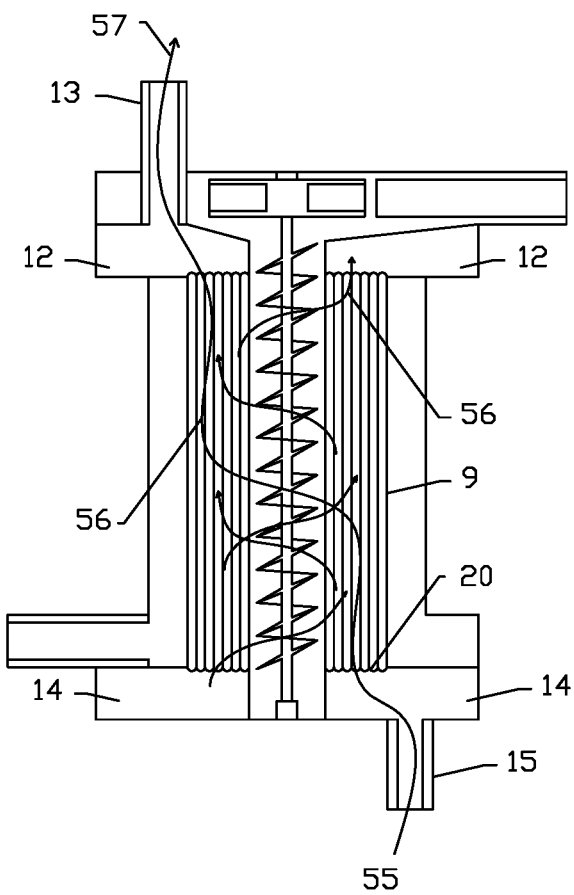

FIG. 10A shows a schematic view of a dialysate flow. An incoming dialysate 52 rotatably is propelled in the open central tubular column 18 from the dialysate inlet subcompartment 4 by the rotary propeller 6 and the longitudinal spiral blade 7 of the axial spiral flow converter. The longitudinal spiral blade 7 pushes the dialysate in a centrifugal direction 53 across the packed bundle of the hollow fibers 9 into the outer circumferential space 8. The dialysate collected in the dialysate outlet subcompartment 10 then flows out (54) through the dialysate output tube 11. FIG. 10B shows a schematic view of a blood flow. An incoming blood 55 flows through the blood intake tube 15 into the blood inlet subcompartment 14, which then goes longitudinally across (56) the individual hollow fibers 20 of the packed bundle of the hollow fibers 9 to the blood outlet subcompartment 12. It then flows out (57) through the blood output tube 13 from the blood outlet subcompartment 12.

Figure 11A:
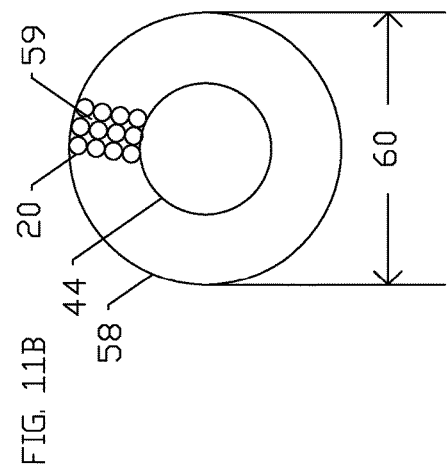
FIGS. 11A-11D show a schematic illustration of reversible radial distension of the packed bundle of the hollow fibers by a centrifugal dialysate flow from a center to a peripheral layer of the packed bundle of the hollow fibers.
Figure 11B:
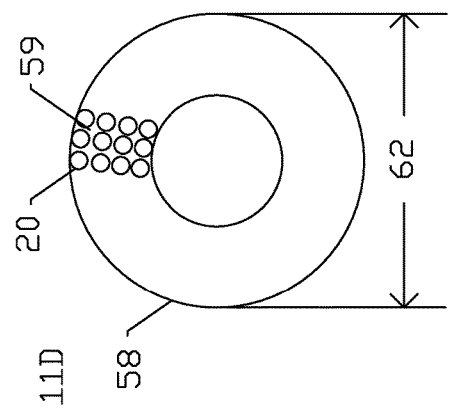
Figure 11C:
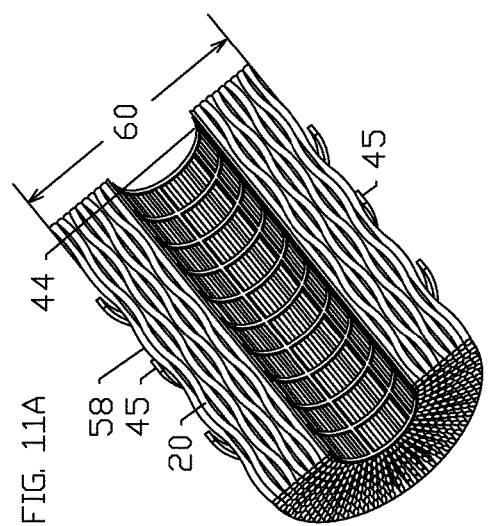
Figure 11D:
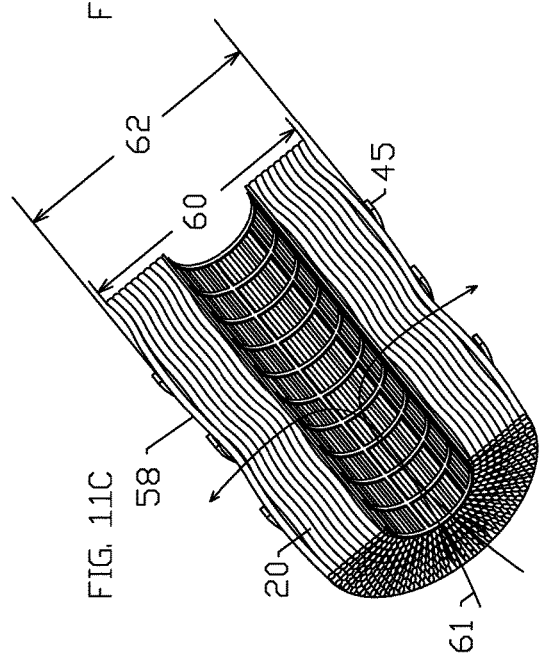

FIG. 11A shows a three dimensional longitudinal cut-out view of the packed bundle of the hollow fibers, comprising the individual hollow fibers 20 concentrically stacked up from around the resiliently stiff inner string harness 44 to an outer circumferential layer 58. The outer circumferential layer 58 of the individual hollow fibers 20 is encased by the elastomeric outer string harness 45. A diameter 60 of an end portion of the packed bundle of the hollow fibers remains unchanged at a mid portion of the packed bundle of the hollow fibers. A cross-sectional view of the packed bundle of the hollow fibers shown in FIG. 11B schematically illustrates the inner string harness 44 and the diameter 60 of the outer circumferential layer 58 of the packed bundle of the hollow fibers in a tightly packed configuration of the individual hollow fibers 20 having an interfibrillar space 59. Shown in FIG. 11C, the elastomeric outer string harness 45 is radially stretched by the centrifugal dialysate flow 61 moving from a central portion to the outer circumferential layer 58 of the packed bundle of the hollow fibers. The centrifugal dialysate flow 61 radially distends the mid portion of the packed bundle of the hollow fibers in a way that a diameter 62 of the mid portion becomes larger than the diameter 60 of the end portion of the packed bundle of the hollow fibers. A cross-sectional view of the packed bundle of the hollow fibers shown in FIG. 11D schematically shows that the larger diameter 62 of the radially distended outer circumferential layer 58 allows the individual hollow fibers 20 to be widely separated apart from other adjacent individual hollow fibers. The wider separation of the individual hollow fibers from each other results in a wider interfibrillar space 59. Once the dialysate flow ceases flowing through the packed bundle of the hollow fibers, the elastomeric outer string harness 45 shrinks back to its resting configuration, the packed bundle of the hollow fibers shrinks to the configuration shown in FIGS. 11A-11B, and the interfibrillar space 59 similarly shrinks back to the configuration shown in FIGS. 11A-11B. The packed bundle of the hollow fibers in a radially distended cross-sectional configuration, which is reversibly produced by the centrifugal dialysate flow, shown in FIGS. 11C-11D allows the dialysate to readily flow centrifugally from the central portion to the outer circumferential layer of the packed bundle of the hollow fibers.

Figure 12A:
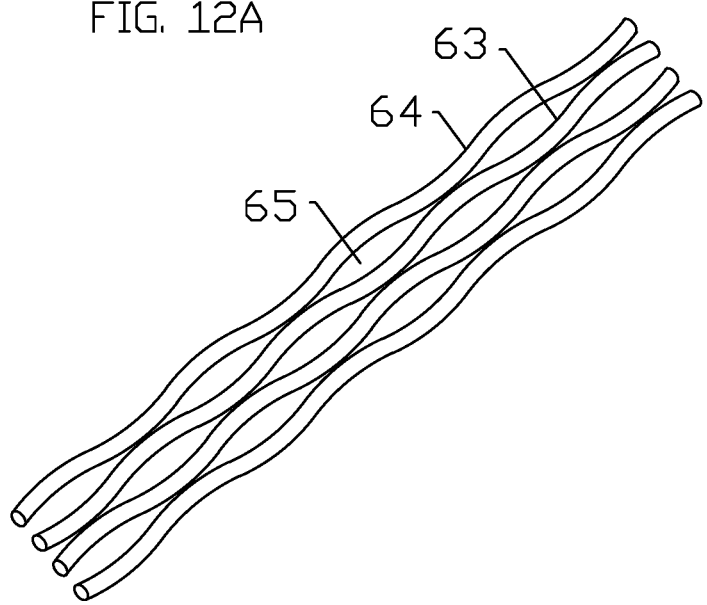
FIGS. 12A-12C schematically illustrate a tortuous tubular configuration of individual hollow fibers.
Figure 12B:
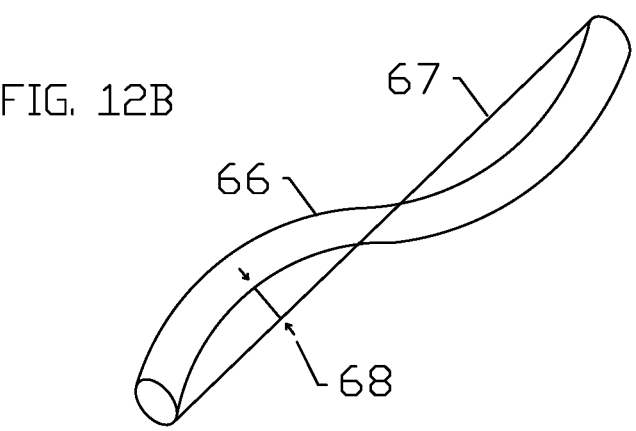
Figure 12C:
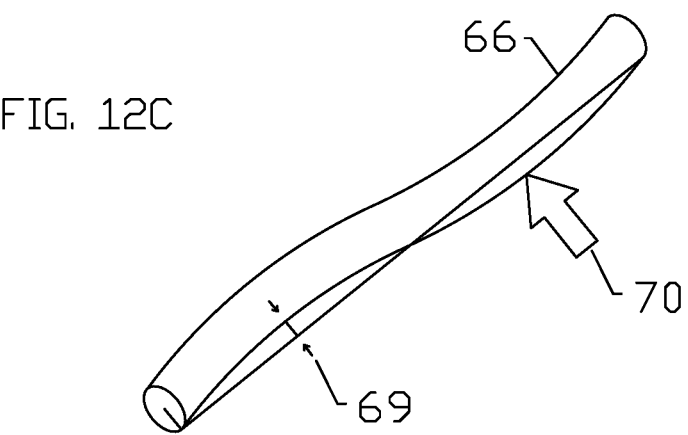

FIG. 12A illustrates a tortuous tubular configuration of individual hollow fibers, stacked up longitudinally together. In between two individual hollow fibers 63 and 64, there is provided an interfibrillar space 65 which is configured to let the dialysate flow through in a substantially tangential angle to a longitudinal axis of the individual hollow fibers. FIGS. 12B and 12C show that an individual hollow fiber 66 is elastomerically stretchable from a maximum deviation (root) 68 to 69 upon a tangential flow 70 of dialysate to a longitudinal axis 67 of the individual hollow fibers 66. The elastomeric stretchability of the individual hollow fibers allows the individual hollow fibers 20 to be radially pushed in a centrifugal direction from the central portion to the outer circumferential layer 58 of the packed bundle of the hollow fibers without material failure such as fracture of the individual hollow fibers upon the tangential flow 70 of the dialysate, shown in FIGS. 11A-11D.

It is to be understood that the aforementioned description of the apparatus is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A centrifugal-dialysate-flow hemodialyzer for hemodialysis, comprising:
    a blood compartment comprising a packed bundle of hollow fibers in a reversibly distensible doughnut configuration on a radial cross-section, wherein the blood compartment is concentrically enclosed in a dialysate compartment;
    the dialysate compartment, provided in a configuration of a compartmentalized tubular cylinder, wherein the dialysate compartment comprises an axial spiral flow converter.

2. The centrifugal-dialysate-flow hemodialyzer for hemodialysis according to claim 1, wherein the blood compartment further comprises:
    a blood inlet subcompartment disposed proximate to a dialysate outlet portion of the centrifugal-dialysate-flow hemodialyzer;
    wherein the blood inlet subcompartment is concentrically divided into an outer tubular columnar space and an inner tubular columnar space by an inner coaxial tubular cylinder of the blood inlet subcompartment;
    wherein the outer tubular columnar space of the blood inlet subcompartment fixedly encases a portion of the packed bundle of the hollow fibers disposed proximate to the blood inlet subcompartment;
    wherein the blood inlet subcompartment is connected to a blood intake tube; and
    wherein the blood inlet subcompartment is configured to transmit blood to the packed bundle of the hollow fibers.

3. The centrifugal-dialysate-flow hemodialyzer for hemodialysis according to claim 1, wherein the blood compartment further comprises:
    a blood outlet subcompartment disposed proximate to a dialysate inlet portion of the centrifugal-dialysate-flow hemodialyzer;
    wherein the blood outlet subcompartment is concentrically divided into an outer tubular columnar space and an inner tubular columnar space by an inner coaxial tubular cylinder of the blood outlet subcompartment;
    wherein the outer tubular columnar space of the blood outlet subcompartment fixedly encases a portion of the packed bundle of the hollow fibers disposed proximate to the blood outlet subcompartment;
    wherein the blood outlet subcompartment is connected to a blood output tube; and
    wherein the blood outlet subcompartment is configured to transmit the blood from the packed bundle of the hollow fibers to the blood output tube.

4. The centrifugal-dialysate-flow hemodialyzer for hemodialysis according to claim 1, wherein the packed bundle of the hollow fibers further comprises:
    an open central tubular column disposed thereof in a central portion of the packed bundle of the hollow fibers along a longitudinal axis of the packed bundle of the hollow fibers;
    wherein the open central tubular column is concentrically surrounded by longitudinally stacked-up individual hollow fibers of the packed bundle of the hollow fibers;
    wherein a portion of the open central tubular column proximate to a blood outlet subcompartment is fixedly encircled by an inner coaxial tubular cylinder of the blood outlet subcompartment;
    wherein a portion of the open central tubular column proximate to a blood inlet subcompartment is fixedly encircled by an inner coaxial tubular cylinder of the blood inlet subcompartment; and
    wherein the open central tubular column is configured to receive dialysate from the inner coaxial tubular cylinder of the blood outlet subcompartment.

5. The centrifugal-dialysate-flow hemodialyzer for hemodialysis according to claim 4, wherein the packed bundle of the hollow fibers further comprises:
    a plurality of individual hollow fibers;
    wherein the individual hollow fiber in a configuration of a tortuous longitudinal tube is elastomerically stretchable along a longitudinal axis of the individual hollow fiber.

6. The centrifugal-dialysate-flow hemodialyzer for hemodialysis according to claim 4, wherein the packed bundle of the hollow fibers further comprises:
    an outer circumferential layer of the packed bundle of the hollow fibers;
    wherein the outer circumferential layer is separated by >1 mm of a radial distance from an inner tubular surface of the dialysate compartment.

7. The centrifugal-dialysate-flow hemodialyzer for hemodialysis according to claim 4, wherein the packed bundle of the hollow fibers further comprises:
    an inner string harness in a tubular configuration, wherein the inner string harness is abuttingly disposed on a perimeter of the open central tubular column, and wherein the inner string harness is configured to be stiff so as to avoid inward collapse of the open central tubular column; and
    an outer string harness in a tubular configuration, wherein the outer string harness is provided to encircle the outer circumferential layer of the packed bundle of the hollow fibers, and wherein the outer string harness is elastomeric and stretchable so as to let the individual hollow fibers of the packed bundle of the hollow fibers be radially dispersed inside the outer string harness by a dialysate flow moving centrifugally from the open central tubular column to the outer circumferential layer.

8. The centrifugal-dialysate-flow hemodialyzer for hemodialysis according to claim 1, wherein the dialysate compartment further comprises:
    a dialysate inlet subcompartment disposed proximate to a blood outlet subcompartment of the centrifugal-dialysate-flow hemodialyzer;
    wherein the dialysate inlet subcompartment rotatably encloses a rotary propeller of the axial spiral flow converter;
    wherein the dialysate inlet subcompartment distally adjoins and opens to an inner coaxial tubular cylinder of the blood outlet subcompartment;

wherein the dialysate inlet subcompartment is distally open to an open central tubular column via the inner coaxial tubular cylinder of the blood outlet subcompartment;

wherein the dialysate inlet subcompartment is connected to a dialysate intake tube; and wherein the dialysate inlet subcompartment is configured to deliver a dialysate to the open central tubular column of the packed bundle of the hollow fibers.

9. The centrifugal-dialysate-flow hemodialyzer for hemodialysis according to claim 1, wherein the dialysate compartment further comprises:

a dialysate outlet subcompartment disposed proximate to a blood inlet subcompartment of the centrifugal-dialysate-flow hemodialyzer;

wherein the dialysate outlet subcompartment proximally adjoins and opens to an outer circumferential space of the dialysate compartment;

wherein the dialysate outlet subcompartment is connected to a dialysate output tube; and wherein the dialysate outlet subcompartment is configured to drain out a dialysate from the outer circumferential space.

10. The centrifugal-dialysate-flow hemodialyzer for hemodialysis according to claim 9, wherein the dialysate compartment further comprises:

the outer circumferential space disposed thereof between a blood outlet subcompartment and the blood inlet subcompartment of the centrifugal-dialysate-flow hemodialyzer;

wherein the outer circumferential space is disposed thereof between an outer circumferential layer of the packed bundle of the hollow fibers and an inner tubular surface of the dialysate compartment;

wherein the outer circumferential space distally adjoins and opens to the dialysate outlet subcompartment; and wherein the outer circumferential space is configured to transmit the dialysate from the outer circumferential space to the dialysate outlet subcompartment.

11. The centrifugal-dialysate-flow hemodialyzer for hemodialysis according to claim 1, wherein the axial spiral flow converter further comprises:

a rotary propeller comprising a set of rotary blades distally adjoining a longitudinal spiral blade;

wherein the rotary propeller is rotatably disposed inside a dialysate inlet subcompartment;

wherein the set of the rotary blades is configured to be passively rotated about a longitudinal axis of a dialysate inlet subcompartment by a dialysate from a dialysate intake tube; and wherein the rotary propeller is configured to rotate the longitudinal spiral blade.

12. The centrifugal-dialysate-flow hemodialyzer for hemodialysis according to claim 11, wherein the axial spiral flow converter further comprises:

the longitudinal spiral blade comprising a single spiral blade fixedly encircling a longitudinal shaft;

wherein the longitudinal spiral blade is coaxially disposed thereof inside an open central tubular column;

wherein a distal tip of the longitudinal spiral blade is rotatably anchored inside an inner tubular columnar space of a blood inlet subcompartment;

wherein the longitudinal spiral blade is configured to coaxially rotate inside the open central tubular column;

wherein the longitudinal spiral blade in a rotating configuration is configured to pull the dialysate in the open central tubular column from the dialysate inlet subcompartment; and wherein the longitudinal spiral blade in the rotating configuration is configured to centrifugally spread the dialysate in the open central tubular column across the packed bundle of the hollow fibers to an outer circumferential space.

* * * * *